(12) United States Patent
Blais et al.

(10) Patent No.: US 9,161,975 B2
(45) Date of Patent: Oct. 20, 2015

(54) IMMUNOGENIC COMPOSITION

(75) Inventors: Normand Blais, Laval (CA);
Anne-Marie Lanteigne, Laval (CA);
Daniel Larocque, Laval (CA); Corey Patrick Mallett, Laval (CA)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 0 days.

(21) Appl. No.: 13/881,932

(22) PCT Filed: Oct. 27, 2011

(86) PCT No.: PCT/EP2011/068832
§ 371 (c)(1),
(2), (4) Date: Apr. 26, 2013

(87) PCT Pub. No.: WO2012/055951
PCT Pub. Date: May 3, 2012

(65) Prior Publication Data
US 2013/0224266 A1    Aug. 29, 2013

Related U.S. Application Data

(60) Provisional application No. 61/407,245, filed on Oct. 27, 2010.

(51) Int. Cl.
| | | |
|---|---|---|
| *A61K 39/39* | (2006.01) | |
| *A61K 9/00* | (2006.01) | |
| *C12P 19/04* | (2006.01) | |
| *A61K 39/145* | (2006.01) | |
| *A61K 39/112* | (2006.01) | |
| *A61K 39/155* | (2006.01) | |
| *A61K 35/74* | (2015.01) | |
| *A61K 39/00* | (2006.01) | |

(52) U.S. Cl.
CPC ............. *A61K 39/39* (2013.01); *A61K 39/0283* (2013.01); *A61K 39/145* (2013.01); *A61K 39/155* (2013.01); *A61K 35/74* (2013.01); *A61K 2039/543* (2013.01); *A61K 2039/55594* (2013.01); *C12N 2760/16134* (2013.01); *C12N 2760/18534* (2013.01)

(58) Field of Classification Search
CPC ..... A61K 35/74; A61K 39/145; A61K 39/39; A61K 2039/543; A61K 39/155; A61K 39/0283; A61K 2039/55594; C12N 2760/16134; C12N 2760/18534
See application file for complete search history.

(56) References Cited

U.S. PATENT DOCUMENTS

| | | | |
|---|---|---|---|
| 7,112,332 B1 | 9/2006 | Lowell | |
| 7,258,863 B2 * | 8/2007 | Oaks et al. | ............... 424/197.11 |
| 7,524,509 B2 * | 4/2009 | Burt et al. | .................. 424/234.1 |

OTHER PUBLICATIONS

Pore et al 2009, Vaccine. Sep. 25, 2009; 27(42):5855-64.*
Mukhopadhaya et al 2003, Vaccine 21 (2003) 3043-3050.*
Fries et al ,Infect Immun 2001 ;69((7)):4545 53.*
Tribble, D et al., "Safely and Immunogenicity of a *Shigella flexneri* 2a Invaplex 50 intranasal Vaccine in adult volunteers", (Aug. 23, 2010) Vaccine, vol. 29, No. 37, pp. 6076-6085.
Coster Trinka S et al., "Vaccination against Shigellosis with Attenuated *Shigella flexneri* 2a strain SC602", (Jul. 7, 1999) Infetion and Immunity, vol. 67, No. 7, pp. 3437-3443.
Mukhopadhaya A et al., "Role of *Shigella flexneri* 2a 34kDa outer membrame protein in induction of protective immune response", (Aug. 14, 2006), Vaccine, vol. 24, No. 33-34, pp. 6028-6036.

* cited by examiner

*Primary Examiner* — Padma V Baskar
(74) *Attorney, Agent, or Firm* — Michael M. Conger

(57) ABSTRACT

The present invention relates to the use of a immunogenic or immunostimulatory composition comprising a *Shigella* outer membrane protein (OMP) and *Shigella* LPS molecule in medicine and methods for preparing the composition.

7 Claims, 14 Drawing Sheets

Fig 1    Stability as Assessed by Particle Size

SFOMP Particle Size over Time at 4C

(Z-Average (d.nm) vs Time (weeks))

Fig 2    Electron Microscopy anti-*S. flexneri* LPS                -- anti-*S. flexneri* LPS Fig 3    Major Proteins in SFOMP, Protollin, and V2 Proteosomes by SDS-PAGE/Coomassie Blue Staining
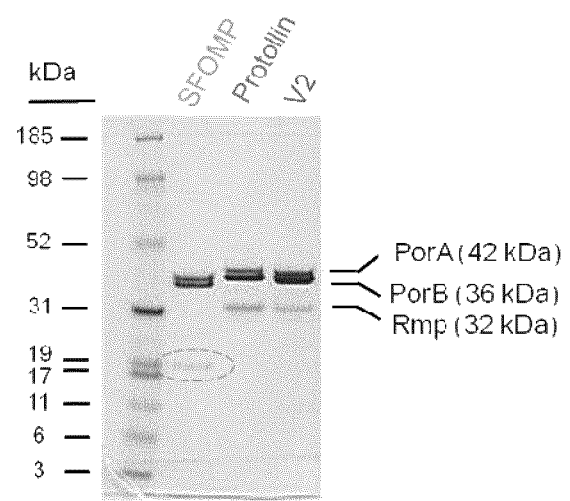

Fig 4    SFOMP Contains TLR1-2 and TLR4 Pathway Agonists Which Trigger Dose-Responsive Activation in a Cell-Based Assay
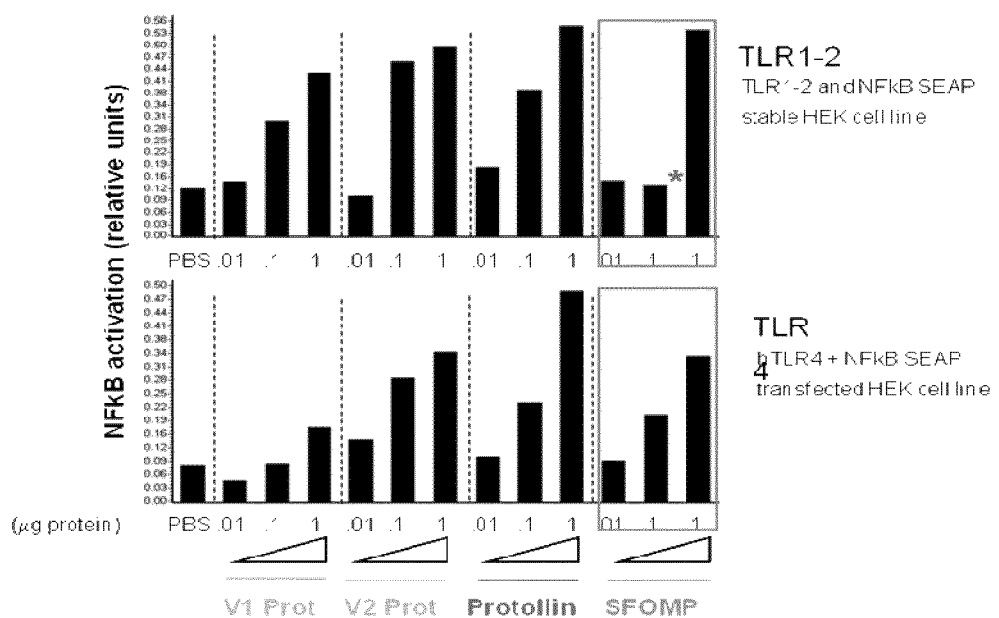

Fig 5a   SFOMP-Adjuvanted preF Antigen Administered Intranasally Protects Mice from RSV Infection
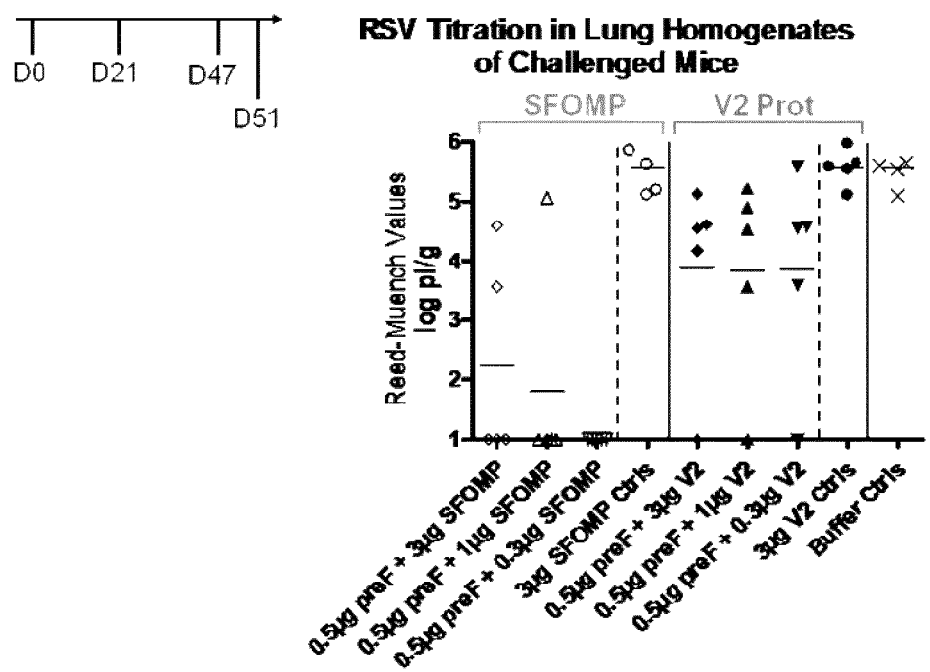

Fig 5b  SFOMP-Adjuvanted preF Antigen Administered Intranasally Protects Mice from RSV Infection
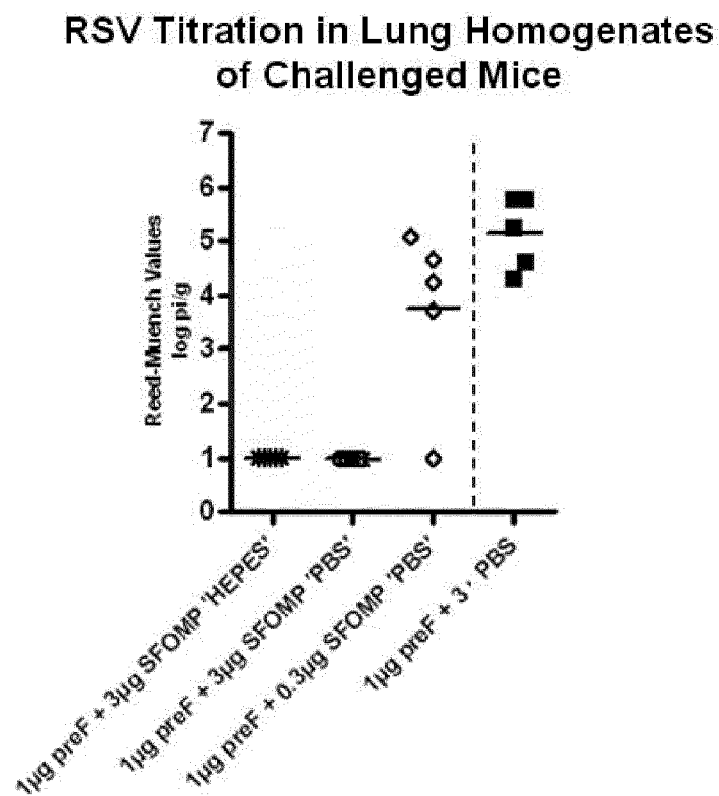

Fig 6  Process to Prepare SFOMP
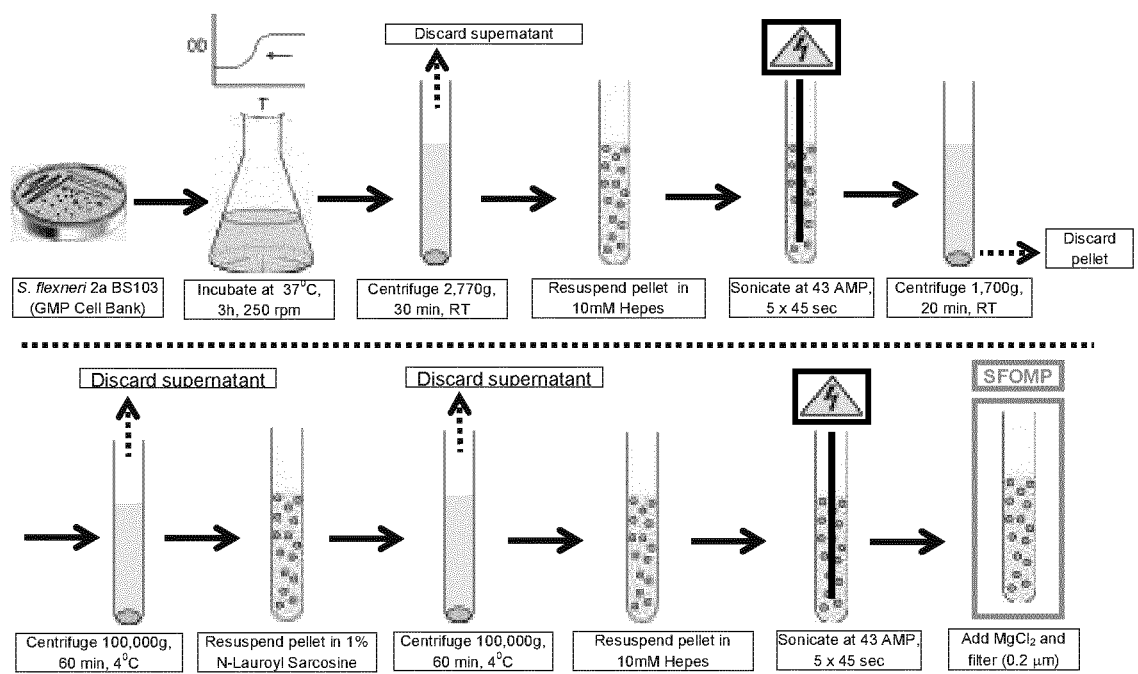

Fig 7    Microarray Analysis of Human Dendritic Cells using SFOMP

| Genes Over-Expressed in SFOmp vs. PBS | | |
|---|---|---|
| Position | Gene Symbol | Fold Regulation |
| A09 | CSF2 (GM-CSF) | 83.7028 |
| A10 | CSF3 (G-CSF) | 188.0702 |
| A11 | CXCL10 | 133.5725 |
| A12 | EIF2AK2 | 8.8521 |
| B09 | IFNB1 | 84.323 |
| B10 | IFNG | 17.9652 |
| B12 | IL10 | 18.9931 |
| C01 | IL12A | 27.329 |
| C02 | IL1A | 15.0308 |
| C03 | IL1B | 11.8343 |
| C05 | IL6 | 160.255 |
| C06 | IL8 | 5.6398 |
| C09 | IRF1 | 6.9174 |
| C12 | LTA | 7.0726 |
| E07 | PELI1 | 5.8977 |
| E10 | PTGS2 | 28.3642 |
| G06 | TNF | 37.2794 |
| H05 | ACTB | 451321.7404 |

| Genes Under-Expressed in Group 1 vs. Control Group | | |
|---|---|---|
| Position | Gene Symbol | Fold Regulation |
| A01 | BTK | -5.32 |
| A06 | CD86 | -4.0754 |
| C10 | IRF3 | -4.7712 |
| D01 | CD180 | -10.2922 |
| F07 | TIRAP | -4.4495 |
| G02 | TLR6 | -4.0531 |
| G07 | TNFRSF1A | -7.1185 |

Fig 8  SFOMP-Adjuvanted preF Antigen Administered Intranasally Elicits Serum and Lung Neutralizing Antibodies Fig 9 Anti-A/New Caledonia HAI Responses in BALB/c Mice following Two IN Immunizations of 3 mg Split-Antigen and Fig 10 Anti-A/New Caledonia Serum IgG Responses in BALB/c Mice following Two IN Immunizations of 3 mg Split-Antigen and 5 mg of Adjuvant
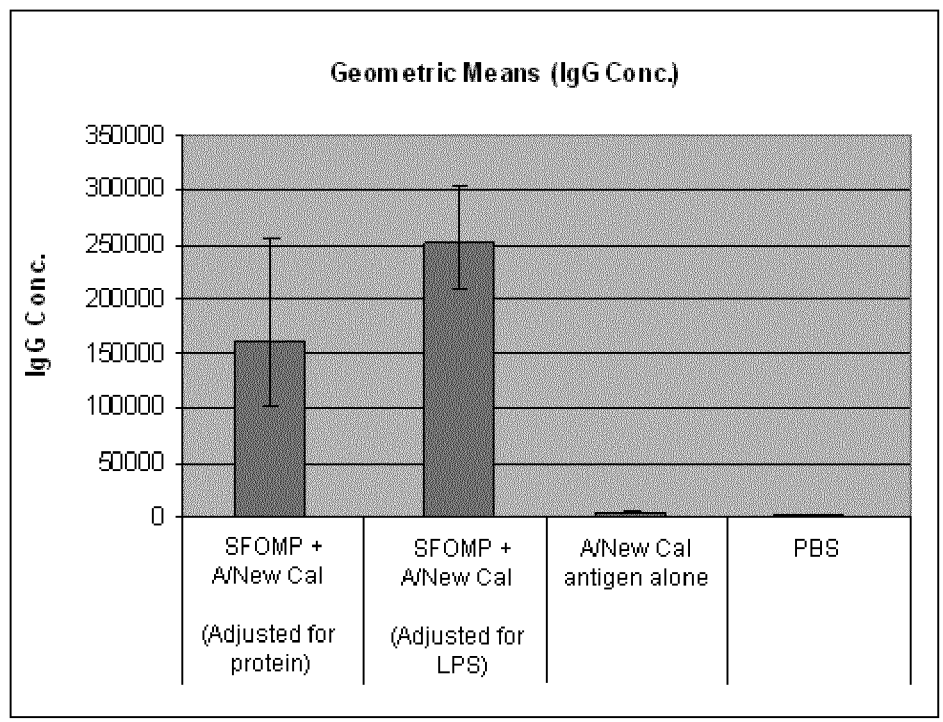

Fig 11 Anti-A/New Caledonia Lung IgA Responses in BALB/c Mice following Two IN Immunizations of 3 mg Split-Antigen and 5 mg of Adjuvant
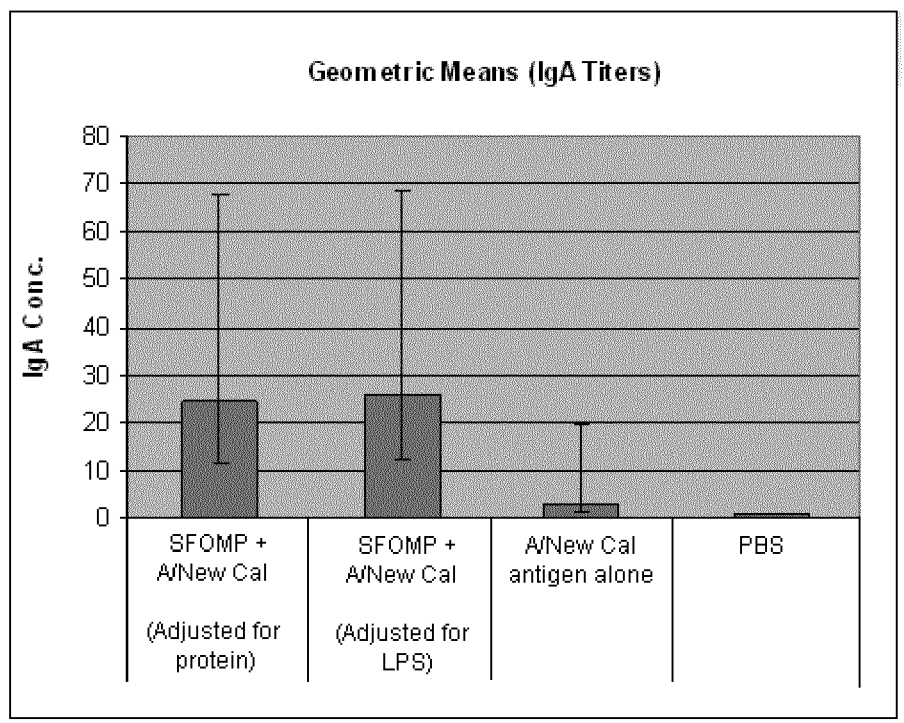

Figure 14.
A
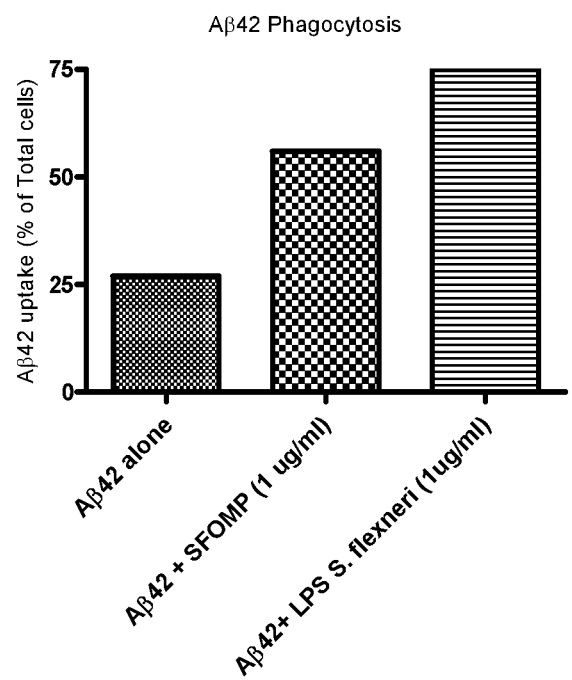
B
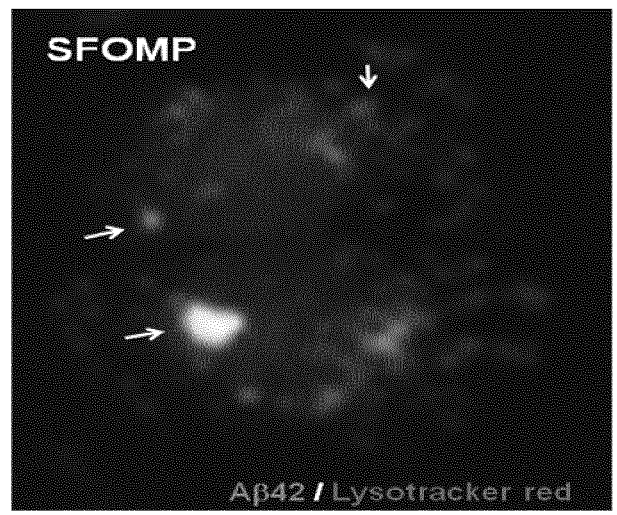

IMMUNOGENIC COMPOSITION

CROSS-REFERENCE TO RELATED APPLICATIONS

This application is filed pursuant to 35 USC 371 as a European National Phase Application of International Patent Application Serial No. PCT/EP2011/068832 filed on Oct. 27, 2011, which claims the benefit of U.S. Provisional 61/407,245 filed Oct. 27, 2010, all of which are incorporated herein in their entirety.

FIELD OF THE INVENTION

The present invention provides compositions, including immunogenic and immunostimulatory compositions, methods for making said compositions, vaccines and methods for making vaccines.

Proteosomes are generally hydrophobic, membranous, multimolecular preparations of meningococcal outer membrane proteins. Proteosome-adjuvanted vaccines have been administered to approximately 2,000 subjects in two clinical programs. Despite a strong safety, immunogenicity, and efficacy record, the use of *Neisseria meningitides* wild-type strain 8047 for proteosome preparation requires enhanced containment (BL-3).

First generation proteosomes originally comprised *N. meningitidis* outer membrane proteins (OMPs), and were used as a vaccine adjuvant.

A *Shigella* vaccine Protollin comprises outer membrane proteins from *N. meningitidis* combined with LPS from *Shigella flexneri* (see Jones et al, Vaccine. 2004 Sep. 9; 22(27-28):3691-7.)

A proteosome production process which produces a combined Neisserial OMP/lipopolysaccharide is disclosed in WO2009132244

Alternative immunogenic and immunostimulatory compositions are still sought, as medicines and adjuvants for medicines.

SUMMARY OF THE INVENTION

In one aspect, the present invention relates to a composition comprising a *Shigella* outer membrane protein (OMP) and *Shigella* LPS molecule.

In one aspect, the present invention relates to a composition produced by a process comprising the steps of:
  growing a *Shigella* strain,
  disrupting the *Shigella* cells; and
  isolating a fraction comprising an outer membrane protein and LPS, suitably by a process involving one or more centrifugation steps and a detergent solubilisation step.

In one aspect, the present invention relates to a method for preparing an immunogenic composition, the method comprising:
  growing a *Shigella* strain;
  disrupting the *Shigella* cells; and
  isolating a fraction comprising an outer membrane protein and LPS suitably by a process involving one or more centrifugation steps and a detergent solubilisation step.

In one aspect, the present invention relates to a composition comprising a *Shigella* outer membrane protein (OMP) and *Shigella* LPS molecule for use in medicine.

In one aspect, the present invention relates to a composition comprising a *Shigella* outer membrane protein (OMP) and *Shigella* LPS molecule for use as a vaccine adjuvant.

In one aspect, the present invention relates to a composition comprising a *Shigella* outer membrane protein (OMP) and *Shigella* LPS molecule for use as a vaccine against *Shigella* infection or disease.

In one aspect, the present invention relates to a composition comprising
1 an antigen capable of eliciting an immune response against an infectious agent, and
2 a *Shigella* outer membrane protein (OMP) and *Shigella* LPS molecule,
for prevention of infection or disease caused by the infectious agent.

In one aspect the present invention relates to the use of a composition comprising a *Shigella* outer membrane protein (OMP) and *Shigella* LPS molecule in medicine.

In one aspect, the present invention relates to the use of a composition comprising a *Shigella* outer membrane protein (OMP) and *Shigella* LPS molecule in the preparation of a vaccine adjuvant.

In one aspect, the present invention relates to the use of a *Shigella* outer membrane protein (OMP) and *Shigella* LPS molecule in the preparation of a vaccine against *Shigella* infection or disease.

In one aspect, the present invention relates to the use of a composition comprising a *Shigella* outer membrane protein (OMP) and *Shigella* LPS molecule in the preparation of a medicament for prevention of infection or disease caused by an infectious agent, the medicament comprising an antigen capable of eliciting an immune response against the infectious agent.

In one aspect, the present invention relates to a method of eliciting an adjuvanted immune response, the method comprising delivery to an individual of a composition comprising a *Shigella* outer membrane protein (OMP) and *Shigella* LPS molecule.

In one aspect, the present invention relates to a method of eliciting an immune response against an infectious agent, the method comprising delivery to an individual in need thereof a composition comprising:
an antigen capable, optionally when adjuvanted, of eliciting an immune response against the infectious agent; and
a composition comprising a *Shigella* outer membrane protein (OMP) and *Shigella* LPS molecule.

In one aspect, the present invention relates to a method of treating or reducing infection or disease caused by an infectious agent, the method comprising delivery to an individual in need thereof a composition comprising an antigen capable of eliciting an immune response protective against infection or disease by the infectious agent, optionally when adjuvanted, the composition comprising a *Shigella* outer membrane protein (OMP) and *Shigella* LPS molecule.

In one aspect, the present invention relates to a kit comprising a *Shigella* outer membrane protein (OMP) and *Shigella* LPS molecule for simultaneous or sequential delivery.

BRIEF DESCRIPTION OF THE DRAWINGS

FIG. 1 Stability as Assessed by Particle Size

FIG. 2 Electron Microscopy

FIG. 3 Major Proteins in SFOMP, Protollin, and V2 Proteosomes by SDS-PAGE/Coomassie Blue Staining FIG. 4 SFOMP Contains TLR1-2 and TLR4 Pathway Agonists Which Trigger Dose-Responsive Activation in a Cell-Based Assay FIG. 5 SFOMP-Adjuvanted preF Antigen Administered Intranasally Protects Mice from RSV Infection FIG. 6 Process to Prepare SFOMP Research Lots for Pilot Adjuvant Studies FIG. 7 Microarray Analysis of Human Dendritic Cells using SFOMP FIG. 8 SFOMP-Adjuvanted preF Antigen Administered Intranasally Elicits Serum and Lung Neutralizing Antibodies FIG. 9 Anti-A/New Caledonia HAI Responses in BALB/c Mice following Two IN Immunizations of 3 mg Split-Antigen and 5 mg of Adjuvant FIG. 10 Anti-A/New Caledonia Serum IgG Responses in BALB/c Mice following Two IN Immunizations of 3 mg Split-Antigen and 5 mg of Adjuvant FIG. 11 Anti-A/New Caledonia Lung IgA Responses in BALB/c Mice following Two IN Immunizations of 3 mg Split-Antigen and 5 mg of Adjuvant

FIG. 14 Aβ42 phagocytosis measured in vitro following the incubation of SFOMP or *S. flexneri* LPS with human mouse microglia cell line (CHME).

DETAILED DESCRIPTION OF THE INVENTION

Figure 12:
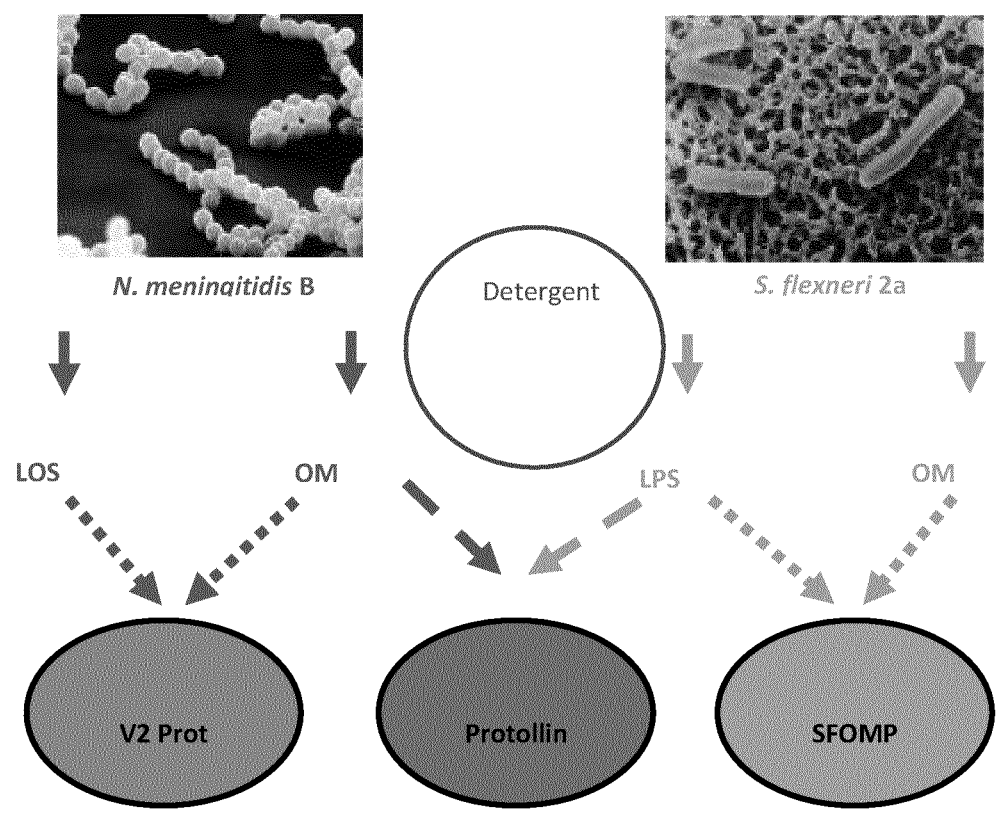
FIG. 12 illustrates the differences between SfOMP, Protollin and V2 Protollin, and is illustrative of LPS/OMP ratios.

The present invention relates to immunogenic and immunostimulatory compositions derived from bacteria, such as *Shigella*.

In one aspect the invention relates to a composition comprising a *Shigella* outer membrane protein (OMP) and a *Shigella* LPS molecule.

In one aspect a composition of the invention is an outer membrane preparation, referred to herein as SFOMP (*Shigella Flexneri* Outer Membrane Protein preparation), produced from *S. flexneri* strain BS103. We have determined that this composition contains LPS and OMPs, as do Protollin and Proteosomes made according to WO2009132244, but has certain advantages over both; namely it is produced from an avirulent strain that requires low containment, it can be produced from 1 fermentation and therefore from 1 process and the theoretical risk of deleterious immune responses to meningitidis group B PS is eliminated. SFOMP also demonstrates enhanced protective effects in comparison to Neisserial LPS/OMP combinations.

The composition of the invention may be an "immunogenic composition", which is capable of priming, potentiating, activating, eliciting, stimulating, augmenting, boosting, amplifying, or enhancing an adaptive (specific) immune response, which may be cellular (T cell) or humoral (B cell), or a combination thereof. Preferably, the adaptive immune response is protective, which may include neutralization of a virus (decreasing or eliminating virus infectivity). A representative example of an immunogen is a microbial antigen (such as one or more RSV antigens or one or more influenza antigens). In this aspect the composition may be used directly as a prophylactic and/or therapeutic agent.

In one aspect the composition of the invention may be an "immunostimulatory composition" which enhances an immune response, suitably enhances the immune response to another antigen, when administered to a mammal, including a human. An immunostimulatory composition may enhance mucosal and/or adaptive immune response and/or cellular and/or humoral immune response and/or innate immune response of the mammal. For instance, an immunostimulatory composition may enhance a mammal's immune response to a specific antigen when co-administered with the antigen. In this aspect the composition may be used as an adjuvant of a prophylactic or therapeutic agent.

Thus compositions of the invention may therefore be useful, for example, as adjuvants for vaccines or as vaccines per se.

The composition of the invention comprises *Shigella* LPS. "LPS," as used herein, refers to native (isolated or prepared synthetically with a native structure) or a modified lipopolysaccharide. Included within the definition of LPS is lipooligosaccharide (LOS), which is generally understood in the art to mean a liposaccharide having a glycan chain consisting of 10 or fewer monosaccharide subunits. LPS also covers lipopolysaccharides which have a glycan chain comprising more than 10 monosaccharide subunits.

A liposaccharide may be in a detoxified form (i.e., having the Lipid A core removed) or may be in a form that has not been detoxified.

Liposaccharides may be endogenous (i.e., naturally contained with the OMP preparation), may be admixed or combined with an OMP preparation from an exogenously prepared liposaccharides (i.e., prepared from a different *Shigella* culture than the OMP preparation, or synthetically), or may be a combination thereof. Such exogenously added LPS may be from the same *Shigella* strain from which the OMP preparation was made or a different *Shigella* strain. In one aspect a composition comprising endogenous LPS is preferred.

The composition comprises an outer membrane protein (OMP). The composition may comprise one, two, three, four or more OMPs. A *Shigella* outer membrane protein is suitably any protein found attached to or associated with the outer membrane of *Shigella* species, suitably a protein having a domain which is considered to be exposed on the outside of the bacterium, and thus visible to the immune system of a human when infected with the bacteria.

Reference to an OMP herein includes variants of naturally occurring OMPs such as deletion, insertion and substitution mutations of that antigen, or other specific variant of that antigen as described herein, or (where the antigen is a polypeptide) to polypeptides having 80% or more, suitably at least 85%, at least 90%, at least 95%, at least 96%, at least 97%, at least 98%, at least 99% identity to that polypeptide, suitably being immunogenic.

In one aspect the composition does not comprise inner membrane proteins.

In another aspect, the *Shigella* OMP and *Shigella* LPS are isolated. By "isolated" it is meant that the *Shigella* OMP and the *Shigella* LPS are separated in part, or substantially, or completely, from one or more of: cytoplasmic cell membrane proteins, and/or DNA, and/or lipid rafts.

In another aspect, the composition is at least 70%, at least 80%, or at least 90% substantially free of inner membrane proteins.

The OMP may be *S. flexneri* OMP 1b, or OMP 3a or OMPX, or combination thereof, in one aspect including all three antigens.

In one aspect of the invention, the outer membrane protein has an acidic pI. The pI for each protein can range between 4.47 and 5.30.

In one aspect the composition of the invention has TLR2 and/or TLR4 pathway agonist activity, and is in one aspect capable of activating one or more components within a cell that are stimulated by TLR2 or TLR4 agonists. In one aspect the TLR agonist activity of the composition is assessed in vitro.

In one aspect, the LPS is a TLR4 pathway agonist. In another aspect, the OMP is a TRL-2 pathway agonist. In one aspect the LPS composition of the invention has TLR4 agonist activity, suitably as assessed using the techniques disclosed in Example 4. By "TLR agonist" or "TLR pathway agonist" it is meant a component which is capable of causing a signaling response through a TLR signaling pathway, either as a direct ligand or indirectly through generation of endogenous or exogenous ligand.

In another aspect, the outer membrane protein has TLR-2 agonist activity, suitably as assessed using the techniques disclosed in Example 4.

In one aspect in the composition does not comprise a *Shigella* housekeeping gene product.

In one aspect compositions have a ratio of LPS to OMP between 0.6:1.3 by weight. The ratio can be 0.8:1.1, such as 0.9:1.

The total protein content of the composition can be measured by such assays as Lowry or bicinchoninic acid (BCA) protein assay kit (Peirce).

In one aspect the *Shigella* strain is *S. flexneri*, but other *Shigella* strains may be used. In one aspect these agents can be handled at low BL1 or BL2 containment levels.

In one aspect the composition is able to upregulate one or more of the following genes: IL6, CSF2; CSF3; CXCL10. Upregulation of a gene is suitably an increase in gene expression in a cell, suitably a dendritic cell, when contacted with the composition of the invention when compared to that gene expression level seen when contacting the same cell with PBS. In one aspect the increase in expression is at least 5 times, at least 10 times, at least 20 times, at least 30 times, at least 40, at least 50, at least 60, at least 70, at least 80, at least 90 times, or even 100 times higher than that seen with PBS. A suitable method for assessing gene expression is given in Example 7.

Compositions of the invention may comprise OMP and/or LPS contained in a vesicle, suitably being a membrane enclosed particulate structure having a measurable diameter.

OMP and LPS may be present with phospholipids such as phosphatidylethanolamine (PE), phosphatidylglycol (PG), phosphatidylcholine (PC), phosphatidylserine (PS), phosphatidylinositol (PI), and cardiolipin (CL), suitably phosphatidylethanolamine (PE) and phosphatidylglycol (PG), which may derive from the *Shigella* as a result of the purification process, or be added to the OMP or LPS.

In one aspect of the invention, the composition comprises particles with a particle size of 30-180 nm in diameter. In one aspect the composition comprises particles with a particle size of not more than 200 nm in diameter. The size of the particles can be measured by measurement of scattered light, for example.

In one aspect of the invention, the particles are stable at 4° C. for 3 months, as determined by measurement of particle size.

Compositions of the invention may also comprise a detergent.

In one aspect the composition of the invention is filterable through a 20 μm filter.

In one aspect the composition comprises an antigen in addition to the OMP and LPS.

In one aspect reference to an antigen herein, including *Shigella* OMP protein or LPS, refers to any agent or substance that stimulates an immune response, either cellular and/or humoral, either alone or in combination or linked or fused to another substance. Antigens are often derived from, or are, foreign microorganisms such as bacteria or viruses, or the substances they produce, including but not limited to peptides, proteins, lipids, carbohydrates, glycoproteins, glycosaminoglycans and complexes of two or more of the above.

An antigen can be a peptide, polypeptide or protein or fragment thereof of at least about 5 amino acids, 10 amino acids, 15 amino acids, 20 amino acids in length or greater. Antigens can be produced artificially by chemical synthesis or molecular biology techniques. Often, artificial antigens are designed to elicit immune responses upon exposure or multiple exposures without the potential consequence of acquiring the disease against which the immune response has been stimulated to protect. The antigen can comprise a "carrier" polypeptide and a hapten, e.g., a fusion protein or a carrier polypeptide fused or linked (chemically or otherwise) to another composition. The antigen can be recombinantly expressed in an immunization vector, which can be simply naked DNA comprising the antigen's coding sequence operably linked to a promoter, e.g., a simple expression cassette.

In one aspect the composition is formulated with one or more antigens by simple admixing.

The additional antigen may be from *Shigella* or a species other than *Shigella*.

In one aspect the antigen is an antigen against which an immune response raised by a human or animal can provide protection against infection or disease, and is preferably a vaccine antigen. In one aspect the antigen is from a microorganism such as a virus, bacteria, fungi or protozoa. In one aspect the antigen is a human antigen, or plant antigen such as a pollen antigen, or antigen selected from an influenza virus, malarial protozoa, HIV, birch pollen, DerP1, grass pollen, RSV, non-typeable *H. influenzae* and Morexella.

Suitable antigens include influenza antigens.

The influenza virus antigen or antigenic preparation thereof may be produced by any of a number of commercially applicable processes. Said influenza virus or antigenic preparation thereof may be derived from the conventional embryonated egg method, by growing influenza virus in eggs and purifying the harvested allantoic fluid egg-derived. Alternatively the influenza virus or antigen preparation thereof may be cell-culture derived using cell or cell culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells or the Per.C6 cell line. Suitable cell substrates are not limited to cell lines; for example primary cells such as chicken embryo fibroblasts and avian cell lines such as chicken or duck cell lines (e.g. EBx cell line such as EB 14 or EB24 derived from chicken or duck embryonic stem cells respectively) are also included. Suitable insect cells are Sf9, Sf2 or Hi5. Alternative cells are yeast cells (such as *Saccharomyces cerevisiae* or *Pichia pastoris*) for recombinant Influenza A antigens for example, or plants.

In one embodiment, an influenza virus or antigenic preparation thereof for use according to the present invention may be a split influenza virus or split virus antigenic preparation thereof. In an alternative embodiment the influenza preparation may contain another type of inactivated influenza antigen, such as inactivated whole virus or purified HA and NA (subunit vaccine), or an influenza virosome. In a still further embodiment, the influenza virus may be a live attenuated influenza preparation. A split influenza virus or split virus antigenic preparation thereof for use according to the present invention is suitably an inactivated virus preparation where virus particles are disrupted with detergents or other reagents to solubilize the lipid envelope. Split virus or split virus antigenic preparations thereof are suitably prepared by fragmentation of whole influenza virus, either infectious or inactivated, with solubilizing concentrations of organic solvents or detergents and subsequent removal of all or the majority of the solubilizing agent and some or most of the viral lipid material. By split virus antigenic preparation thereof is meant a split virus preparation which may have undergone some degree of purification compared to the split virus whilst retaining most of the antigenic properties of the split virus components. For example, when produced in eggs, the split virus may be depleted from egg-contaminating proteins, or when produced in cell culture, the split virus may be depleted from host cell contaminants. A split virus antigenic preparation may comprise split virus antigenic components of more than one viral strain. Vaccines containing split virus (called 'influenza split vaccine') or split virus antigenic preparations generally contain residual matrix protein and nucleoprotein and sometimes lipid, as well as the membrane envelope proteins. Such split virus vaccines will usually contain most or all of the virus structural proteins although not necessarily in the same proportions as they occur in the whole virus. Examples of commercially available split vaccines are for example FLUARIX™, FLUSHIELD™, or FLUZONE™. Split flu may be produced using a solvent/detergent treatment, such as tri-w-butyl phosphate, or diethylether in combination with Tween™ (known as "Tween-ether" splitting) of by using other splitting agents including detergents or proteolytic enzymes or bile salts, for example sodium deoxycholate. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including Triton X-IOO (for example in a process described in Lina et al, 2000, Biologicals 28, 95-103) and Triton N-101, or combinations of any two or more detergents. The preparation process for a split vaccine may include a number of different filtration and/or other separation steps such as ultracentrifugation, ultrafiltration, zonal centrifugation and chromatography (e.g. ion exchange) steps in a variety of combinations, and optionally an inactivation step eg with heat, formaldehyde or β-propiolactone or U. V. or any combination thereof which may be carried out before or after splitting. The splitting process may be carried out as a batch, continuous or semi-continuous process. A preferred splitting and purification process for a split immunogenic composition is described in WO 02/097072. Preferred split flu vaccine antigen preparations according to the invention comprise a residual amount of Tween 80 and/or Triton X-100 remaining from the production process, although these may be added or their concentrations adjusted after preparation of the split antigen. In one embodiment of both Tween 80 and Triton X-100 are present. The preferred ranges for the final concentrations of these non-ionic surfactants in the vaccine dose, arising from the antigenic preparation, are:

Tween 80: 0.01 to 1%, or about 0.1% (v/v)

Triton X-100: 0.001 to 0.1 (% w/v), or 0.005 to 0.02% (w/v). Alternatively, the influenza virus may be in the form of a whole virus vaccine.

This form may prove to be an advantage over a split virus vaccine for a pandemic situation as it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation. In addition to the greater degree of certainty with a whole virus approach, there is also a greater vaccine production capacity than for split virus since considerable amounts of antigen are lost during additional purification steps necessary for preparing a suitable split vaccine.

In another embodiment, the influenza virus preparation is in the form of a purified sub-unit influenza vaccine. Sub-unit influenza vaccines generally contain the two major envelope proteins, HA and NA, and may have an additional advantage over whole virion vaccines as they are generally less reactogenic, particularly in young vaccinees. Sub-unit vaccines can be produced either recombinantly or purified from disrupted viral particles. Examples of commercially available sub-unit vaccines are for example AGRIPPAL™, or FLUVIRTN™. In a specific embodiment, sub-unit vaccines are prepared from at least one major envelope component such as from haemagglutinin (HA), neuraminidase (NA), or M2, suitably from HA. Suitably they comprise combinations of two antigens or more, such as a combination of at least two of the influenza structural proteins HA, NA, Matrix 1 (M1) and M2, suitably a combination of both HA and NA, optionally comprising MI. Suitably, the influenza components are produced by recombinant DNA technology, i.e. results from, or is expressed from, a nucleic acid resulting from recombinant DNA manipulations, including live recombinant vector (vaccinia) or recombinant subunit protein (baculovirus/insect cells, mammalian cells, avian cells, yeast, plants or bacteria). Suitable insect cells are *Spodoptera frugiperda* (Sf9) insect cells or High Five (Hi5) insect cells developed from *Trichoplusia ni* (Invitrogen) and suitable baculovirus are *Autographa californica* nuclear polyhedrosis virus (AcNPV) (Baculogold, Becton Dickinson, PharMingen) or the so-called Bacmid system.

In one embodiment, the influenza virus preparation is in the form of a virosome.

Virosomes are spherical, unilamellar vesicles which retain the functional viral envelope glycoproteins HA and NA in authentic conformation, intercalated in the virosomes' phospholipids bilayer membrane. Examples of commercially available virosomal vaccines are for example INFLEXAL V™, or INVA VAC™.

In another embodiment, the sub-unit influenza components are expressed in the form of virus-like-particles (VLP) or capsomers, suitably plant-made or insect cells-made VLPs. VLPs present the antigens in their native form. The VLP sub-unit technology may be based entirely on influenza proteins, or may rely on other virus such as the murine leukaemia virus (MLV) and may therefore comprise a non-influenza antigen such as MLV gag protein. A suitable VLP comprises at least one, suitably at least two influenza proteins, optionally with other influenza or non-influenza proteins, such as MI and HA, HA and NA, HA, NA and MI or HA, NA and MLV gag. It may be produced either in plant cells or insect cells. VLPs can also carry antigens from more than one influenza strain, such as VLPs made from two seasonal strains (e.g. HINI and H3N2) or from one seasonal and one pandemic strain (e.g. H3N2 and H5N1) for example.

Accordingly, in one embodiment the immunogenic compositions and uses thereof according to the invention comprise an influenza virus antigen or antigenic preparation thereof from influenza virus grown on eggs or on cell culture. In another embodiment, said influenza virus antigen or antigenic preparation thereof comprises a whole virus, a split virus, a virosome or one or more purified antigen chosen from: HA, NA, M1, M2. In another embodiment, said purified antigen(s) are prepared from influenza virus grown in mammalian, avian or insect cells. Specifically, said purified antigen(s) are recombinantly produced. They can be in the form of a Virus-like-particle.

The influenza virus strain may be a reassortant strain, produced by classical reassortant techniques or by reverse genetics techniques, with the reassortant virus being rescued in the presence of in the absence of a helper virus. These techniques are well known in the art.

When influenza virus is cell-derived, the amount of residual host cell DNA is reduced to low levels, in order to minimize the tumourigenic potential of the vaccine. Host cell DNA will normally not exceed 10 ng per dose of vaccine, and suitably be less than 1 ng, less than 100 pg, less than 50 pg or less than 25 pg per dose. Validated methods used to assess residual DNA levels are for example: blotting techniques or quantitative PCR, e.g. Southern blot, slot blots, the Threshold™ system from Molecular devices.

In one embodiment, the influenza preparation is prepared in the presence of low level of thiomersal, or in the absence of thiomersal. In another embodiment, the resulting influenza preparation is stable in the absence of organomercurial preservatives, in particular the preparation contains no residual thiomersal. In particular the influenza virus preparation comprises a haemagglutinin antigen stabilized in the absence of thiomersal, or at low levels of thiomersal (generally 5 µg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072.

The invention can be operated with vaccine including interpandemic, pandemic or pre-pandemic influenza strains. The vaccines may include influenza virus strains which are not strictly matching the then circulating strain, and are effective for example against "influenza drift variant", i.e. new strains that have changed enough to cause an epidemic again among the general population; through a process termed "antigenic drift."

Suitably the influenza virus strain or strains to be included in the immunogenic or vaccine composition is/are interpandemic (seasonal) strain(s), i.e. circulating influenza viruses that are related to those from the preceding epidemic, or strain(s) being associated with a pandemic outbreak or having the potential to be associated with a pandemic outbreak (herein a "pre-pandemic strain"). Different strains may be included in a multivalent composition, such as a mixture of interpandemic strains, a mixture of pandemic strains or a mixture of both.

Interpandemic strains are for example strains which circulate globally during interpandemic periods such as but not limited to: HINI, H1N2, H3N2 or B. Commercially available influenza vaccines are a trivalent combination including one influenza B strain and two influenza A strains (HINI, H3N2). A suitable composition therefore contains antigens prepared from the three WHO recommended strains of the appropriate influenza season, usually two influenza A virus strains and one influenza B strain. A standard 0.5 ml injectable dose in most cases contains (at least) 15 µg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and Immunoelectrophoresis techniques for the assay of haemagglutinin antigen of influenza virus. J. Biol. Stand. 9 (1981) 317-330). Another suitable composition contains four influenza strains such as the three classical strains, and an additional B strain (Commun Dis Intel) 2006, 30, 350-357) or an additional H3N2 strain (Vaccine 1992, 10, 506-511).

Another suitable composition for use in the present invention comprises a pandemic influenza strain, or an influenza strain susceptible to be associated with a pandemic, in the form of a monovalent pandemic or pre-pandemic composition, alone, in combination or in addition to one or more seasonal (i.e. interpandemic) strains. Pandemic or pre-pandemic strains are for example from an avian or pig origin.

The features of an influenza virus strain that give it the potential to cause a pandemic or an outbreak of influenza disease associated with pandemic influenza strains are: (i) the influenza virus must undergo a major change that results in a completely new virus (eg a new haemagglutinin as compared to haemagglutinin of currently circulating strains); (ii) the new virus is pathogenic for humans and (iii) the new virus must be transmissible from human to human. A new haemagglutinin may emerge at unpredictable levels with a totally different subtype from strains circulating the season before, with resulting antigens varying from 20% to 50% from the corresponding protein of strains that were previously circulating in humans, through a phenomenon called "antigenic shift" which results in virus escaping 'herd immunity' and establishing pandemics. Therefore the new HA has not been evident in the human population for an extended period of time, probably a number of decades, such as H2. Or it may be a haemagglutinin that has not been circulating in the human population before, for example H5, H9, H7 or H6 which are found in avian species (birds). In either case the majority, or at least a large proportion of, or even the entire population has not previously encountered the antigen and is immunologically naïve to it. At present, the influenza A virus that has been identified by the WHO as one that potentially could cause a pandemic in humans is the highly pathogenic H5N1 avian influenza virus. Therefore, the pandemic vaccine according to the invention will suitably comprise H5N1 virus. Two other suitable strains for inclusion into the claimed composition are H9N2 or H7N1.

Suitably the vaccines for use in the invention will include any one of the following 16 HA subtypes (HI-H 16) and/or any one of the nine NA subtypes (N1-N9) that have been identified for influenza A viruses. Suitably the vaccine will include a HA and a NA moiety, but the vaccine can also include an antigen from a recombinant origin, in this case it may be HA only, or it may be any combination of one or more of HA, NA, M1, and M2. Suitably three seasonal (e.g. HINI, H3N2, B) strains are present. Suitably four strains are present that are from the group of: four seasonal strains (e.g. HINI, H3N2, two B strains; or HINI, B, two H3N2 strains) or the group of one pandemic (e.g. avian) strain plus three seasonal strains (e.g. HINI, H3N2, B). Suitable A strains are, but not limited to: interpandemic strains such as: HINI, H3N2, and pandemic strains or strains susceptible to be associated with a pandemics for example strains having at least one of the H5, H2, H7, H9 or H10 subtype, specifically H2N2, H5N1, H5N2, H5N3, H5N8, H5N9, H7N1, H7N2, H7N3, H7N4, H7N7, H9N2 and H10N7. Within a given subtype, different variant are possible, such as within the H5 subtype the following variants are: clade 1, clade 2, clade 3 etc.

Suitably the HA is from at least three, at least four influenza strains. One or two B strains from two different lineage (such as B/yamagata or B/Victoria) may be included.

In specific embodiments, the immunogenic composition contains (i) an haemagglutinin (HA) from a single influenza strain, referred to as a "monovalent" influenza composition;

or (ii) a HA from more than one influenza strain, referred to as a "multivalent" influenza composition.

A suitable multivalent composition for use according to the invention is a bivalent composition comprising haemagglutinin (HA) from two influenza virus strains such as but not exclusively two strains associated to a pandemic or susceptible to be associated with a pandemic, e.g. H5 or H2, a trivalent composition comprising HA from three influenza virus strains, optionally from two A strains, and one B strain such as but not limited to B/Yamagata or B/Victoria, a quadrivalent composition comprising haemagglutinin (HA) from four influenza virus strains or a pentavalent composition comprising haemagglutinin (HA) from five influenza virus strains. A suitable quadrivalent composition comprises haemagglutinin from two A strains and two B strains from different lineage (such as B/Yamagata or B/Victoria). Alternatively a quadrivalent composition comprises haemagglutinin from three A strains (optionally HlNl, H3N2, and one A strain associated to a pandemic or susceptible to be associated to a pandemic) and one B strain (such as B/Yamagata or B/Victoria). Another alternative quadrivalent composition comprises haemagglutinin from four interpandemic A strain, or from four A strains at least one of which being associated to a pandemic or susceptible to be associated to a pandemic, such as avian strains such as H5+H2+H7+H9. Specifically a multivalent adjuvanted pandemic composition such as a pandemic bi-valent (e.g. H5+H2) or trivalent or quadrivalent (e.g. H5+H2+H7+H9) offers the advantage of a pre-emptive immunisation against pandemic influenza A threats subtypes and durable priming against threat subtypes. Optionally, such a pandemic vaccine may be combined with a seasonal vaccine. A multivalent composition can also comprise more than 5 influenza strains such as 6, 7, 8, 9 or 10 influenza strains. When two B strains are used in a multivalent seasonal composition, they can suitably be from two different lineages (optionally from B/Victoria and B/Yamagata). At least one of said B strain, suitably both B strains, will be from a circulating lineage. Such a composition is particularly suitable for children.

Suitably the HA per strain is at the usual 15 μg HA per strain, as determined by Single Radial Immunodiffusion (SRID). The HA per strain may alternatively be a low amount of HA (optionally 10 μg HA per strain or below). Suitably the HA per strain is at about or below 5 μg, at about 2.5 μg or below. Said low amount of HA may be as low as practically feasible provided that it allows to formulate a vaccine which fulfils the requirements of the binding Pharmacopeia such as the international e.g. EMEA or FDA criteria for efficacy, as detailed below (see Tables 1 and 2 and the specific parameters as set forth). The amount of HA per strain can be as little as 3.8 μg per human vaccine dose, or even as little as 1.9 μg per dose. A vaccine dose of 0.5 ml is suitably used. Advantageously, a vaccine dose according to the invention, in particular but not exclusively a low HA amount vaccine, may be provided in a smaller volume than the conventional injected split flu vaccines, which are generally about 0.5, 0.7 or 1 ml per dose. The low volume doses according to the invention are suitably below 500 μl, typically below 300 μl and suitably not more than about 200 μl or less per dose. A dose volume of 0.2 ml is suitable for intranasal administration and may be administered in two fractions of 0.1 ml per nostril. Slight adaptation of the dose volume will be made routinely depending on the HA concentration in the original bulk sample, or depending on the delivery route with smaller doses being given by the intranasal or intradermal route, or depending on the target population (for example infants may receive half of an adult human dose).

The influenza medicament of the invention suitably meets certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). Note for harmonization of requirements for influenza vaccines, 1997 CHMP/BWP/214/96 circular N° 96-0666: 1-22) for clinical trials related to annual licensing procedures of influenza vaccines (Table 3). The requirements are different for adult populations (18-60 years) and elderly populations (>60 years) (Table 3). For the annual re-registration of interpandemic influenza vaccines, at least one of the assessments (seroconversion factor, seroconversion rate, seroprotection rate) should meet the European requirements, for all strains of influenza included in the vaccine. The proportion of HI titres equal or greater than 1:40 is regarded most relevant because these titres are expected to be the best correlate of protection [Beyer W et al. 1998. Clin Drug Invest.; 15: I-12].

As specified in the "Guideline on dossier structure and content for pandemic influenza vaccine marketing authorization application. (CHMP/VEG/4717/03, Apr. 5, 2004, or more recently EMEA/CHMP/VWP/263499/2006 of 24 Jan. 2007 entitled 'Guidelines on flu vaccines prepared from viruses with a potential to cause a pandemic', available on www.emea.e-u.int)" issued by the European Medicines Agency's Committee, in the absence of specific criteria for influenza vaccines derived from non circulating strains, it is anticipated that a pandemic candidate vaccine should (at least) be able to elicit sufficient immunological responses to meet suitably all three of the current standards set for existing vaccines in unprimed adults or elderly subjects, after two doses of vaccine. The EMEA Guideline describes the situation that in case of a pandemic the population will be immunologically naive and therefore it is anticipated that all three CHMP criteria for seasonal vaccines should be fulfilled by pandemic candidate vaccines. No explicit requirement to prove it in pre-vaccination seronegative subjects is required. However, Guidance for pre-pandemic vaccine expects that for vaccines used for primary immunisation of a previously immunologically naive population, influenza vaccines used for pandemic preparedness should induce high seroprotection rates, preferably after one or at most two doses. All three criteria (seroprotection rate, GMT increase and response rate) as defined in guideline CPMP/BWP/214/96 should be fulfilled.

The compositions for use in the present invention suitably meet at least one such criteria for the strain included in the composition (one criteria is enough to obtain approval), suitably at least two, or typically at least all three criteria for protection as set forth in Table 1.

TABLE 1

| (CHMP criteria) | | |
|---|---|---|
| | 18-60 years | >60 years |
| Seroconversion rate* | >40% | >30% |
| Seroconversion factor** | >2.5 | >2.0 |
| Seroprotection rate*** | >70% | >60% |

*Seroconversion rate is defined as the proportion of subjects in each group having a protective post-vaccination titre ≥1:40. The seroconversion simply put is the % of subjects who have an HI titre before vaccination of <1:10 and ≥1:40 after vaccination. However, if the intial titre is ≥1:10 then there needs to be at least a fourfold increase in the amount of antibody after vaccination.
**Seroconversion factor is defined as the fold increase in serum HI geometric mean titres (GMTs) after vaccination, for each vaccine strain.
***Seroprotection rate is defined as the proportion of subjects who have a (protective) post-vaccination HI titre of ≥1:40; it is normally accepted as indicating a degree of protection.

A 70% seroprotection rate is defined by the European Medicines Agency's Committee for Medicinal Products for Human Use (CHMP) as one of three criteria normally required to be met for an annual seasonal influenza vaccine and which CHMP is also expecting a pandemic candidate vaccine to meet. However, mathematical modeling has indicated that a vaccine that is, at the population level, only 30% efficient against certain drifted strains may also be of benefit in helping to reduce the magnitude of a pandemic and that a pandemic vaccination campaign using a (pre-pandemic) vaccine with 30% efficacy against infection (30% reduction in susceptibility) against the pandemic strain (cross-protection of 30%) could effectively reduce the clinical attack rate by 75% and consequently morbidity/mortality within the population (Ferguson et al, Nature 2006).

The U.S. FDA has published a draft guidance (CBER draft criteria) (available from the Office of Communication, Training and Manufacturers Assistance (HFM-40), 1401 Rockville Pike, Suite 200N, Rockville, Md. 20852-1448, or by calling 1-800-835-4709 or 301-827-1800, or from the Internet at http://www.fda.gov/cber/guidelines.htm) on Clinical Data Needed to Support the Licensure of Pandemic Influenza Vaccines, and the proposed criteria are also based on the CHMP criteria. FDA uses slightly different age cut-off points. Appropriate endpoints similarly include: 1) the percent of subjects achieving an HI antibody titer>1:40, and 2) rates of seroconversion, defined as a fourfold rise in HI antibody titer post-vaccination. The geometric mean titer (GMT) should be included in the results, but the data should include not only the point estimate, but also the lower bound of the 95% confidence interval of the incidence rate of seroconversion, and the day 42 incidence rate of HI titers>1:40 must exceed the target value. These data and the 95% confidence intervals (CI) of the point estimates of these evaluations should therefore be provided. FDA draft guidance requires that both targets be met. These FDA-issued criteria are summarized in Table 2.

TABLE 2

(CBER draft criteria)

|  | 18-60 years | >60 years |
| --- | --- | --- |
| Seroconversion rate* | >40% | >30% |
| Rate of HI titres ≥1:40 | >70% | >60% |

*Seroconversion rate is defined as a) for subjects with a baseline titre ≥1:10, a 4-fold or greater rise; or b) for subjects with a baseline titre <1:10, a rise to ≥1:40.
These criteria must be met at the lower bound of the 95% CI for the true value.

Accordingly, in one aspect of the invention, it is provided the vaccine composition will be able to induce an immune response against influenza virus which meets at least one criteria, suitably two, suitably all three criteria for protection set out above. Specifically at least one of the following criteria is met for the or all strains present in the vaccine after one single dose. Accordingly there is also provided a one dose intranasal influenza vaccine, or a low amount influenza vaccine, wherein the adjuvant is herein defined.

Populations to vaccinate are children, adults and elderly. The target population to vaccinate is the entire population, e.g. healthy young adults (e.g. aged 18-50 or 18-60), elderly (typically aged above 60) or infants/children/adolescents. The target population may in particular be naïve, or immuno-compromised or immuno-suppressed. Immunocompromised or immuno-suppressed humans generally are less well able to respond to an antigen, in particular to an influenza antigen, in comparison to healthy adults. In a specific aspect, the vaccine is administered intranasally. Typically, the vaccine is administered locally to the nasopharyngeal area, suitably without being inhaled into the lungs. It is desirable to use an intranasal delivery device which delivers the vaccine formulation to the nasopharyngeal area, without or substantially without it entering the lungs. Suitable devices for intranasal administration of the vaccines according to the invention are spray devices. Suitable commercially available nasal spray devices include Accuspray™ (Becton Dickinson). Nebulisers produce a very fine spray which can be easily inhaled into the lungs and therefore does not efficiently reach the nasal mucosa. Nebulisers are therefore not preferred. Suitable spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO91/13281 and EP311863B and EP516636, incorporated herein by reference. Such devices are commercially available from Pfeiffer GmbH and are also described in Bommer, R. Pharmaceutical Technology Europe, September 1999. Suitable intranasal devices produce droplets (measured using water as the liquid) in the range 1 to 200 μm, suitably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is a further suitable feature of an intranasal delivery system for use with the vaccines according to the invention. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a mono-dose device may be used for administering the vaccines according to the invention.

Thus, the invention provides in one aspect the use of a non-live influenza virus antigen preparation and an adjuvanted as herein defined in the manufacture of a vaccine formulation for a one-dose nasal vaccination against influenza. The vaccine may be administered in a mono-dose format or a bi-dose format (generally one sub-dose, optionally of 0.1 ml each, for each nostril).

In another aspect, the invention provides in another aspect the use of a low dose of non-live influenza virus antigen and an adjuvant as herein defined in the manufacture of a mucosal vaccine for immunisation against influenza. Although the vaccine of the invention may be administered as a single dose, components thereof may also be co-administered together at the same time or at different times (for instance influenza antigens could be administered separately, suitably at the same time as the administration of the adjuvant). In addition to a single route of administration, 2 different routes of administration may be used when two injections are administered. For example, the first administration (e.g. priming dose) of adjuvanted influenza antigens may be administered IM (or ID) and the second administration (e.g. booster dose) may be administered IN (or ID). In addition, the vaccines of the invention may be administered IM for priming doses and IN for booster doses, or vice versa.

In a further aspect, the invention provides a pharmaceutical kit comprising an intranasal spray device and a one-dose influenza virus vaccine. Suitably the one-dose influenza vaccine is non-live, optionally a split virus vaccine. Suitably the device is a bi-dose delivery device for two sub-doses of vaccine, optionally for two sub-doses of 0.1 ml each of vaccine.

In one aspect the composition additionally comprises a pharmaceutically acceptable excipient to form a pharmaceutical composition. In one aspect an "excipient" as used herein refers to any substance added to a composition that is not responsible for the principle activity of the composition. Excipients may be used to increase the stability, consistency or deliverability of the active ingredient, for example. Excipients, as used herein, may include diluents or carriers.

The invention relates to a method for preparing an immunogenic composition, the method comprising
growing a *Shigella* strain,
disrupting the *Shigella* cells; and
isolating a fraction comprising an outer membrane protein and LPS by a process involving the separation of the outer from the inner membrane protein.

In one aspect, the process involves one or more centrifugation steps.

In one aspect, the process involves a detergent solubilisation step.

In one aspect, the separation of the outer from the inner membrane protein is provided by the selective solubilisation of cytoplasmic inner membrane proteins.

The invention relates to products made by processes of the invention.

In one aspect the process comprises two or more centrifugation steps.

In one aspect the process comprises disruption of cells by sonication, suitably at 45 AMP, 5×45 seconds and/or for 5×60 seconds. In another aspect cells may be disrupted by homogenisation or other mechanical means.

In one aspect, the process comprises removing the cell debris from the cell mixture of the disrupted *Shigella* cells by at least one method selected from centrifugation, filtration, depth filtration or anion exchange chromatography.

In another aspect isolation of a fraction comprising an outer membrane protein and LPS comprises one or more steps selected from centrifugation, filtration, depth filtration or anion exchange chromatography.

In one aspect the process comprises 2 sonication steps, for cell disruption and for disrupting aggregates that may form, to make a homogenous composition.

In one aspect the process comprises solubilisation of cellular membrane proteins by N-Lauroyl sarcosine. Alternative detergents that may be used include one or more of: lauryl dimethylbetaine (LDB), sodium deoxycholate (DOC), Lauryldimethylamine-oxide (LDAO), Cetyltrimethylammoniumbromide (CTAB), Sodium dodecylsulfate (SDS), N-Laurolysarcosine, Sodium octyl sulfate, Triton, Trizma® dodecyl sulfate, Nonidet™ P 40, Pentaethylene glycol and derivatives, Polyoxyethylene (20) sorbitan monolaurate, Polyoxyethylene 40 stearate, Saponin, TWEEN® 20 and related substances, Decanoyl-N-methylglucamide (Mega-10), 3-[(3-Cholamidopropyl)dimethylammonio]-2-hydroxy-1-propanesulfonate (CHAPSO), Sorbitan monolaurate (Span-20), Polyoxyethylene[23]lauryl ether (BRIJ) and Dimethyloctylphosphine oxide (APO). In some aspects of the present invention, only about 200 ppm of detergent, or less, is used to keep the OMP-based immunostimulant soluble.

In particular, the present invention provides a method of preparing an composition comprising the steps of: *Shigella* is grown at 37° C., cells are centrifuged at 2,770 g, 30 min at RT, the supernatant is discarded, the pellet is resuspended in 10 mM Hepes, sonication at 43 AMP, 5×45 sec. The resuspension is centrifuged at 1,700 g, 20 min, RT, the pellet is discarded, and supernatant centrifuged at 100,000 g, 60 min, 4° C. The supernatant is discarded and the pellet is resuspended in 1% N-Lauroyl Sarcosine, then centrifuged at 100,000 g, 60 min, 4° C. The supernatant is discarded, and the pellet is resuspended in 10 mM Hepes, sonicated at 43 AMP, 5×45 sec (electricity), $MgCl_2$ is added and filtered (0.2 um).

In one aspect of the present invention, said *Shigella* bacteria are engineered bacteria. Bacteria can be engineered to overexpress certain and/or engineered to underexpress at least one other protein. Bacteria can be engineered by various methods known in the art including site directed mutagenesis, or disruption or deletion of part or all of an encoding gene. Bacteria can also be engineered to over or under express certain polypeptides such as outer membrane proteins when cultured under selective growth conditions. Furthermore, and as understood in the art, bacteria can be engineered by the addition of certain encoding sequences into the genome of the bacteria or by expression vector.

In one aspect the *Shigella* strain is *S. flexneri*, optionally *S. flexneri* 2a BS103. Other *Shigella species* and *S. flexneri* strains may be also used.

In one aspect the *Shigella* strain is a non pathogenic strain, capable of being grown under BL1 or BL2 conditions. In one aspect the composition of the invention can be produced under BL1 or BL2 conditions.

In one aspect the *Shigella* species has reduced virulence or toxicity with respect the wild type *Shigella*. Suitably the *Shigella* species can be grown and manipulated in BL1 or BL2 facilities, and does not need BL3 or higher facilities. In one aspect the virulence and/or toxicity of the strain is modified by genetic manipulation. In another aspect a strain is selected with reduced virulence and/or toxicity. In one aspect the strain has an LPS mutation.

In one aspect the invention relates to a composition comprising a *Shigella* outer membrane protein (OMP) and *Shigella* LPS molecule for use in medicine.

In one aspect the invention relates to a composition comprising a *Shigella* outer membrane protein (OMP) and *Shigella* LPS molecule for use as a vaccine adjuvant.

In one aspect the invention relates to a composition comprising a *Shigella* outer membrane protein (OMP) and *Shigella* LPS molecule for use as a mucosal vaccine adjuvant.

In one aspect the invention relates to a composition comprising a *Shigella* outer membrane protein (OMP) and *Shigella* LPS molecule for use as a vaccine against *Shigella* infection or disease.

In one aspect the invention relates to a composition comprising 1 an antigen capable of eliciting an immune response against an infectious agent, and 2 a *Shigella* outer membrane protein (OMP) and *Shigella* LPS molecule, for prevention of infection or disease caused by the infectious agent.

In one aspect the invention relates to a composition comprising 1 an antigen, and 2 a *Shigella* outer membrane protein (OMP) and *Shigella* LPS molecule In one aspect the invention relates to a composition comprising a *Shigella* outer membrane protein (OMP) and *Shigella* LPS molecule for use in medicine.

In one aspect the invention relates to the use of a composition comprising a *Shigella* outer membrane protein (OMP) and *Shigella* LPS molecule in the preparation of an adjuvant.

In one aspect the invention relates to the use of a composition comprising a *Shigella* outer membrane protein (OMP) and *Shigella* LPS molecule in the preparation of a mucosal adjuvant.

In one aspect the invention relates to the use of a *Shigella* outer membrane protein (OMP) and *Shigella* LPS molecule in the preparation of a vaccine against *Shigella* infection or disease.

In one aspect the invention relates to the use of a *Shigella* outer membrane protein (OMP) and *Shigella* LPS molecule in the preparation of a vaccine against infection or disease.

In one aspect the invention relates to the use of a composition comprising a *Shigella* outer membrane protein (OMP) and *Shigella* LPS molecule in the preparation of a medicament for prevention of infection or disease caused by an infectious agent, the medicament comprising an antigen capable of eliciting an immune response against the infectious agent.

In one aspect the invention relates to a method of eliciting an adjuvanted immune response, the method comprising delivery to an individual a composition comprising a *Shigella* outer membrane protein (OMP) and *Shigella* LPS molecule.

In one aspect the invention relates to a method of eliciting an immune response against an infectious agent, the method comprising delivery to an individual in need thereof a composition comprising:

an antigen capable of eliciting an immune response against the infectious agent and a composition comprising a *Shigella* outer membrane protein (OMP) and *Shigella* LPS molecule.

In one aspect the invention relates to a method of treating/reducing/ameliorating infection or disease caused by an infectious agent, the method comprising delivery to an individual in need thereof a pharmaceutical composition comprising an antigen capable of eliciting an immune response protective against infection or disease by the infectious agent, the pharmaceutical composition comprising a *Shigella* outer membrane protein (OMP) and *Shigella* LPS molecule.

In one aspect the invention relates to a method wherein the infectious agent is bacterial or viral, eg influenza, or RSV.

In one aspect the invention relates to a method in which the antigen capable of eliciting an immune response protective against infection or disease is RSV F/G, or Influenza HA/NA. In another aspect, the antigen is derived from house dust mites, Grass pollen, Ragweed pollen, cats, trees, molds and foods.

The antigen used may be at least a whole or disrupted microorganism. The microorganism may be selected from virus, bacteria, fungi and protozoa. The antigen may be from influenza virus. The antigen may comprise at least one hemagglutinin; it may be monovalent or trivalent. Additionally, antigens may comprise a fragment and/or variant and/or hybrid antigen from the group of: human antigens such as cancer antigens, influenza virus, malarial protozoa, HIV, birch pollen, DerPI, grass pollen, RSV, non-typeable *H. influenzae* and Morexella. Antigens may be recombinant antigens or synthetic antigens and/or a hybrid/chimeric antigens.

In one aspect the invention relates to a method of treating/reducing/amelioriating infection by *Shigella* comprising delivery to an individual in need thereof a composition as disclosed herein.

In one aspect the invention relates to a method wherein the pharmaceutical composition is delivered by the intranasal route or other mucosal route.

Immunostimulatory and immunogenic compositions and vaccines of the present invention may be used as treatment for an existing disease or prophylactically to prevent the occurrence or worsening of a disease.

In one aspect the invention relates to a kit comprising a *Shigella* outer membrane protein (OMP) and *Shigella* LPS molecule for simultaneous, substantially simultaneous or sequential delivery.

The compositions and/or immunogenic compositions of the present invention can be administered by a route selected from: oral, intranasal, sublingual, rectal, intramuscular, intravenous, intraperitoneal, mucosal, enteral, parenteral and inhalation. The mucosal route is via the nasal, oropharyngeal, ocular or genitourinary mucosa.

In another aspect, administering said composition to a mammal induces an innate immune response against infections, including viral and bacterial infections.

Where an antigen is provided then the amount of antigen in the composition is suitably selected as an amount which induces an immunogenic response or immunostimulatory effect. Such amount will vary depending upon the specific components used and how they are presented. Generally, it is expected that each dose will comprise 1-100 μg of protein antigen or OMV preparation, suitably 5-50 μg, and most typically in the range 5-25 μg.

An optimal amount for a particular composition can be ascertained by standard studies involving observation of appropriate immune responses in subjects.

Following an initial dose of a composition of the invention, subjects may receive one or several booster doses adequately spaced.

The efficacy of vaccines can be assessed through a variety of assays. Protection assays in animal models are well known in the art.

A further aspect of the invention relates to immunogenic compositions comprising an outer membrane protein (OMP) and an LPS molecule, suitably both from an avirulent strain of an otherwise pathogenic organism, which composition is suitably capable of eliciting an immune response against the pathogenic organism.

In a different aspect, the present invention relates to immunogenic compositions comprising an outer membrane protein (OMP) and an LPS molecule, from any suitable species, made according to the process of the present invention. In one aspect, a suitable species is selected from the group of (1) prokaryotes, including but not limited to, (a) Bacteria(l)(um), meaning a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii,*

*Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, (b) an archaeon, including but not limited to Archaebacter, and (2) a unicellular or filamentous eukaryote, including but not limited to, a protozoan, a fungus, a member of the genus *Saccharomyces, Kluveromyces,* or *Candida*, and a member of the species *Saccharomyces ceriviseae, Kluveromyces lactis,* or *Candida albicans*.

In a different aspect the invention relates to a composition comprising at least one *Shigella* outer membrane protein, and said composition for use in treatment or prevention of disease, either directly or as an adjuvant to another component.

In yet another aspect the invention relates to a method of preventing and/or reducing amyloid deposition or Alzheimer's disease in a subject comprising treatment of a subject with a composition described herein, and the composition of the invention for use in preventing and/or reducing amyloid deposition or Alzheimer's disease. In one aspect the composition is SFOMP made as in Example 6 herein.

We have determined that the activity of human microglial cells in the phagocytosis of beta amyloid 1-42 is increased by the SFOMP composition as made in example 6 herein. SFOMP specifically increases the level of phagocytosis of beta-amyloid 1-42 peptide by human microglial cells when compared with the delivery of Beta amyloid alone (27% of cells contain beta amyloid vs 56% of cells containing beta amyloid when using SFOMP).

In addition, Sfomp (at a 5 ug dose of LPS per mouse) can increase the percentage of lineage negative CD11b positive monocytes in the blood in C57BL6 mice by a factor of three fold, when compared to PBS. These calls are considered important in the development of microglia in the brain capable of phagocytosis of beta amyloid.

As used herein, "amyloid" encompasses any insoluble fibrous protein aggregate that is deposited in the body. Amyloid deposition may be organ-specific (e.g. central nervous system, pancreas, etc.) or systemic.

In accordance with this aspect of the invention, amyloidogenic proteins subject to deposition include beta protein precursor, prion, [alpha]-synuclein, tau, ABri precursor protein, ADan precursor protein, amylin, apolipoprotein AI, apolipoprotein AII, lyzozyme, cystatin C, gelsolin, protein, atrial natriuretic factor, calcitonin, keratoepithelin, lactoferrin, immunoglobulin light chains, transthyretin, A amyloidosis, [beta]2-microglobulin, immunoglobulin heavy chains, fibrinogen alpha chains, prolactin, keratin, and medin. Amyloid deposition may occur as its own entity or as a result of another illness (e.g. multiple myeloma, chronic infection, or chronic inflammatory disease).

Therefore, the methods of the present invention can further be used to treat a subject having a condition or disease that is associated with, or resulting from, the deposition of amyloidogenic proteins. Such conditions include, but are not limited to, Alzheimer's disease, diffuse Lewy body disease, Down syndrome, hereditary cerebral hemorrhage with amyloidosis, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, dialysis-associated amyloidosis, systemic amyloidosis, and familial systemic amyloidosis.

Treatment or prevention of Alzheimers disease, is a preferred feature of the invention.

In this aspect the invention relates to method of preventing or treating disease in a subject. In one aspect the subject for prevention or treatment may have already been diagnosed with symptoms of a disease characterised by amyloid deposition. In one aspect the subject for treatment has not already been diagnosed with symptoms of a disease characterised by amyloid deposition.

In one aspect the present invention relates to an effect on the deposits of amyloid protein, and in another aspect to an effect on behaviours that are associated with disease states, and in particular prevention or reduction of behaviours associated with Alzheimer's disease.

In one aspect the methods and compositions of the invention have an effect both on amyloid protein deposition and behaviour associated with disease, such as behaviour associated with Alzheimer's disease, although in another aspect the methods and compositions of the invention have an effect either at the level of amyloid deposits or at the level of behaviour.

In one aspect the prevention or reduction in severity of Alzheimer's disease comprises prevention or reduction of loss of memory. In a further aspect the invention relates to relates to improvement in memory. The memory may be spatial memory.

In one further aspect the invention relates to use of compositions as disclosed herein for improved phagocytosis of Amyloid beta.

In one aspect the invention relates to use of compositions as disclosed herein for stimulation of microglial cell activity.

In one aspect the invention relates to the use of compositions comprising a *Shigella* outer membrane protein (OMP) and *Shigella* LPS molecule in combination with an antigen, for example a polypeptide or part thereof or mimetic, such as beta amyloid. Where beta amyloid is used then an N terminal fragment may be used, such as a fragment starting at any of amino acids 1, 2, 3, 4, 5, 6, 7, 8, 9, or 10 and ending at amino acid 6, 7, 8, 9, 10, 11, 12, 13, 14 or 15, having at least 5 amino acids.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Embodiments herein relating to "vaccine compositions" of the disclosure are also applicable to embodiments relating to "immunogenic compositions" of the disclosure, and vice versa.

The term "about" (or "around") in all numerical values allows for a 5% variation, i.e. a value of about 1.25% would mean from between 1.19%-1.31%.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of particular embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims. It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine study, numerous equivalents to the specific procedures described herein. Such equivalents are considered to be within the scope of this disclosure and are covered by the claims. All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

Any aspect of the disclosure may be combinable with any other aspect of the disclosure, unless such a combination of features is otherwise apparent from the context.

The disclosure will be further described by reference to the following, non-limiting, examples:

EXAMPLE 1

Stability of SFOMP as Assessed by Particle Size, and Characterisation of Particles SFOMP particles were made according to the process of Example 6, and mean diameter over time assessed by measurement of scattered light. FIG. 1.

Particle sizes were stable at 4 degrees C. over 3 months.
Mean Protein to LPS ratios varied from (0.7-1.1): 1, as shown in Table 3.

TABLE 3

Summary of SFOMP Research Lots and Pilot Stability and Electron Microscopy Data

| N | Mean Protein:LPS Ratio | Mean Particle Size | Mean Detergent Concentration |
|---|---|---|---|
| 8 | 0.9:1 (0.7-1.1:1) | 155 (140-170) | <20 ppm |

EXAMPLE 2

Electron Microscopy (EM)

EM of SFOMP particles made according to Example 6 show that S. flexneri comprises LPS in the outer membrane of the particles, as measured by anti-S. flexneri LPS antibody binding. FIG. 2.

EXAMPLE 3

Major Proteins in SFOMP, Protollin, and V2 Proteosomes by SDS-PAGE/Coomassie Blue Staining SFOMP particles were made according to the process of Example 6 and compared by gel electrophoresis using standard techniques with V2 proteosomes and Protollin (the latter comprising N. meningitidis OMP and Shigella LPS, for example as disclosed in U.S. Patent Application Publication No. 2003/0044425).

As shown in FIG. 3, the OMPs in SFOMP differ from the OMPs in Protollin and V2 Proteosomes. SFOMP preparations comprise OMP1b, OMP3a and OMPX. Table 4

TABLE 4

Summary of MS/MS Identification of Three Major Proteins in SFOMP

| Protein | MW (kDa) | PI | Structure | Function |
|---|---|---|---|---|
| OMP 1b | 40 | 4.47 | 16 transmembrane b-sheets | active transport |
| OMP 3a | 35 | 5.31 | 1) OmpA-like transmembrane domain 2) OmpA globular, periplasmic family domain | cellular structure |
| OMP X | 18 | 5.30 | 8 transmembrane b-sheets | host cell adhesion |

EXAMPLE 4

SFOMP Contains TLR1-2 and TLR4 Pathway Agonists which Trigger Dose-Responsive Activation in a Cell-Based Assay HEK cells were treated with SFOMP, Protollin, and V1 and V2 Proteosomes. V1 proteosomes contain only N. meningitidis OMPs, whereas V2 contains LPS in addition. Protollin contains N. meningitidis OMPs and S. flexneri LPS.

NFkB is activated in TLR1-2 Human Embryonic Kidney (HEK) cells by treatment with SFOMP in a dose dependent manner, showing that SFOMP comprises a TLR1-2 agonist. FIG. 4.

NFkB is activated in TLR4 Hek cells by treatment with SFOMP in a dose dependent manner, showing that SFOMP comprises a TLR-4 agonist.

EXAMPLE 5

SFOMP-Adjuvanted preF Antigen Administered Intranasally Protects Mice from RSV Infection Mice were vaccinated intranasally at D0 and D21 with RSF protein F and either V2 protesomes or SFOMP made according to example 6. Mice were then challenged at day 47 with RSV virus and sacrificed at day 51. Lung homogenates of challenged mice were tested to see the LD50 value of the virus.

Results are shown in FIG. 5

SFOMP alone was not effective against RSV infection but significantly improved the protection when compared to the F antigen alone and the V2 proteosome.

EXAMPLE 6

Preparation of SFOMP Research Lots for Pilot Adjuvant Studies

Cells used were *S. flexneri* 2a BS103 (GMP Cell Bank) grown with shaking at 3 h, 250 rp, at 37° C. Cells were centrifuged at 2,770 g, 30 min, RT; and the supernatant was discarded. The pellet was resuspended in 10 mM Hepes. The cells were sonicated at 43 AMP, 5×45 sec. Cells were centrifuged at 1,700 g, 20 min, RT, and the pellet was discarded. The supernatant was centrifuged at 100,000 g, 60 min, 4° C.; and the supernatant was discarded. The pellet was resuspended in 1% N-Lauroyl Sarcosine. The resuspension was centrifuged at 100,000 g, 60 min, 4° C.; and the supernatant was discarded. The pellet was resuspended in 10 mM Hepes, and sonicated at 43 AMP, 5×45 sec. $MgCl_2$ was added and filter (0.2 μm) was carried out. The composition arising is referred to herein as SFOMP. FIG. 6.

EXAMPLE 7

Microarray Analysis of Human Dendritic Cells Using SFOMP

Gene expression in dendritic cells expression was assessed by microarray analysis of human dendritic cells. Results are shown in FIG. 7. SFOMP is able to cause upregulation and downregulation of certain genes in dendritic cells in comparison to dendritic cells treated with PBS buffer.

EXAMPLE 8

SFOMP-Adjuvanted preF Antigen Administered Intranasally Elicits Serum and Lung Neutralizing Antibodies 1 μg RSV pre F antigen was combined with 3 or 0.3 μg of SFOMP and delivered intranasally to mice. Neutralizing antibodies were obtained. (FIG. 8)

EXAMPLE 9

Responses in BALB/c Mice Following Two IN Immunizations of 3 mg Split-Antigen and 5 mg of Adjuvant Immune Responses were assessed in mice following two intranasal immunizations of 3 mg influenza split-Antigen and 5 mg of SFOMP Adjuvant. Geometeric mean antibody titres were assessed against HA, and also IgG and IgA. The flu New Caledonian A strain was used to produce the split antigen. Geometeric mean titres (GMTs) were determined. SFOMP+ antigen gave a significantly improved response when compared with PBS alone or antigen alone. (FIGS. 9, 10 and 11)

FIG. 12*illustrates* the differences between SfOMP, Protollin and V2 Protollin, and illustrative LPs/OMP ratios.

EXAMPLE 10

Figure 13:
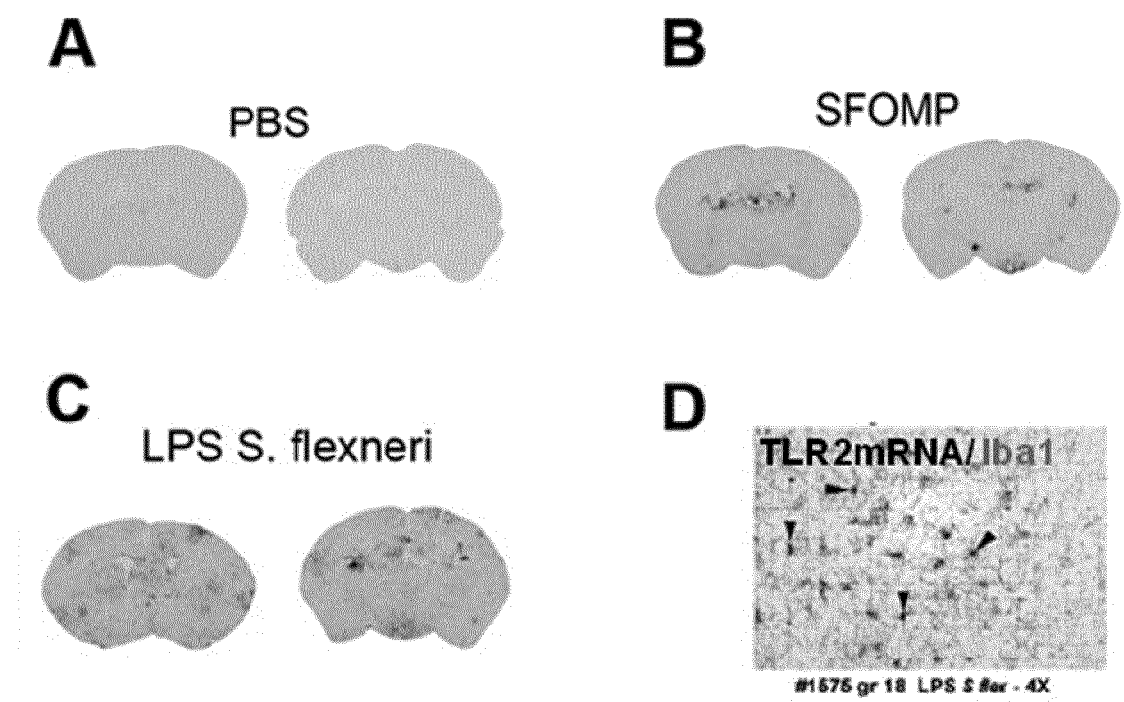
FIG. 13 Innate activation within the brain 24 hours following the intraperitoneal injection of SFOMP (1 ug per mouse) or *Shigella flexneri* lipopolysaccharides (LPS) at 1 ug dose in C57BL/6 mice.

Innate Activation within the Brain 24 Hours Following the Intraperitoneal Injection of SFOMP (1 μg Per Mouse) or *Shigella flexneri* Lipopolysaccharides (LPS) at 1 μg Dose in C57BL/6 Mice. FIG. 13

Innate activation is denoted by the presence of TLR2 mRNA measured by in situ hybridization. Black deposits around the brain ventricular regions shows that TLR2 mRNA is present in the brain of mice injected with SFOMP (B) compared to the negative control (A). Brains from *S. flexneri* LPS injected mice show that innate activation is also demonstrated within the brain parenchyma, cortical and ventricular regions (C). Iba1 immunohistochemistry on TLR2 in situ hybridization micrograph exhibits that TLR2 mRNA is mainly present in microglia cells (Iba1+ cells).

EXAMPLE 11

Aβ42 phagocytosis measured in vitro following the incubation of SFOMP or *S. flexneri* LPS with human mouse microglia cell line (CHME). FIG. 14. Aβ42 peptide is labeled with Hi-Lyte Fluo488 (Anaspec Inc.) and used at 1 ug/ml. A time point of 24 hrs is sufficient to observe an Aβ42 uptake for 56% of the cells after the incubation with SFOMP or at the level of 75% compared to the negative control (Aβ42 peptide alone) (FIG. 14 A). Aβ42 peptide following their uptake is located within the lysosome (lysotracker red) indicating that Aβ42 peptides are phagocytosed. A representative picture following the SFOMP incubation is shown (FIG. 14B). Arrows are pointing co-localization of Aβ42 peptide and the lysosome marker (lysotracker).

The invention claimed is:

1. An immunogenic composition comprising (i) a *Shigella flexneri* outer membrane protein (OMP) wherein the *Shigella flexneri* OMP is selected from the group consisting of OMP 1b, OMP 3a and OMPX, (ii) *Shigella flexneri* LPS molecule, and (iii) an additional antigen from, Respiratory Syncytial Virus (RSV) envelope proteins or influenza virus envelope proteins wherein the composition is a filtered composition and wherein the ratio of LPS to OMP is between 0.6:1.3 and 0.8:1.1.

2. A composition according to claim 1, wherein the LPS is a TLR4 pathway agonist.

3. A composition according to claim 1, wherein the OMP is a TLR2 pathway agonist.

4. A composition according to claim 1, wherein the ratio of LPS to OMP is 0.9:1.

5. A composition according to claim 1, wherein the composition is able to upregulate one or more of the following genes in dendritic cells: IL6, CSF2; CSF3; CXCL10.

6. A composition according to claim 1, additionally comprising a pharmaceutically acceptable excipient to form a pharmaceutical composition.

7. A composition according to claim 1 produced by a process comprising the steps of growing a *Shigella* strain, disrupting the *Shigella* cells; and isolating a fraction comprising an outer membrane protein and LPS.

* * * * *